United States Patent [19]

Harbulak

[11] 4,310,389
[45] Jan. 12, 1982

[54] METHOD FOR SIMULTANEOUS DETERMINATION OF THICKNESS AND ELECTROCHEMICAL POTENTIAL IN MULTILAYER PLATED DEPOSITS

[75] Inventor: Edward P. Harbulak, Allen Park, Mich.

[73] Assignee: Chrysler Corporation, Highland Park, Mich.

[21] Appl. No.: 159,547

[22] Filed: Jun. 16, 1980

[51] Int. Cl.³ .................... G01N 27/02; G01N 27/26
[52] U.S. Cl. .............................. 204/1 T; 204/129.2; 204/129.6; 204/195 R; 204/224 R; 324/71 R

[58] Field of Search .................. 204/1 T, 1 C, 195 R, 204/195 C, 195 F, 129.2, 129.6, 224 R, 224 M; 324/71 R

[56] References Cited

U.S. PATENT DOCUMENTS 2,457,234  12/1948  Herbert et al. ............... 204/195 R
4,179,349  12/1979  Park .............................. 204/195 R Primary Examiner—G. L. Kaplan
Attorney, Agent, or Firm—Newtson & Dundas

[57] ABSTRACT

A method and apparatus for simultaneously measuring the thickness of individual layers of a multilayer plated deposit, the electrochemical potential difference between the layers, and the relative polarity of the layers, is disclosed.

3 Claims, 2 Drawing Figures

METHOD FOR SIMULTANEOUS DETERMINATION OF THICKNESS AND ELECTROCHEMICAL POTENTIAL IN MULTILAYER PLATED DEPOSITS

BACKGROUND OF THE INVENTION

1. Field of Invention

The present invention relates generally to the electrochemical plating of articles and more particularly to means for testing the efficacy of such plating.

2. Description of the Prior Art

The automotive industry makes widespread use of decorative chromium plated parts on exterior surfaces. It is common industry practice to plate such parts in multiple layers employing duplex nickel and chromium to protect the base material of the part from corrosion while presenting an attractive appearance.

The prevention of premature failure of the protective plating layers to perform this function is a matter of extensive, expensive, and continuous effort in the industry. To this end certain criteria have been developed for evaluating the long term corrosion resistance of duplex nickel and chromium plated parts. Among these are adequate nickel thickness, appropriate ratio of semibright to bright nickel thickness, and satisfactory electrochemical potential difference and polarity between the semibright and bright nickel layers.

Suitable means to measure the total thickness of the combined nickel layers such as by deplating (coulometric stripping) is well known and widely used in the industry. The necessity for determination of the individual nickel layer thicknesses and thickness ratio, however, while well known, involves the use of microscopic techniques which are both tedious and time consuming. Use of such techniques is therefore rather expensive and consequently use in the prior art has been severely limited. Even more laborious and difficult to determine is interlayer electrochemical potential difference and polarity, which consequently has meant that such determinations have practically never been made. This nondetermination of a relevant criterion has often resulted in misdiagnosis of the failure mechanism of a prematurely corroded part.

SUMMARY OF THE INVENTION

Responsive to the deficiencies in the prior art it is an object of the present invention to provide simple, rapid, and economical means for determining the corrosion resistance of a multilayer plated part.

According to a feature of the present invention, means are provided for simultaneously measuring the thickness of individual plate layers, thickness ratio, electrochemical potential difference between layers, and clarity of the various layers during the deplating of a multilayer plated sample.

BRIEF DESCRIPTION OF THE DRAWINGS

These and other objects and features will become apparent to those skilled in the plating arts upon reading the following detailed description with reference to the accompanying drawing in which.

DESCRIPTION OF THE PREFERRED EMBODIMENT

Figure 1:
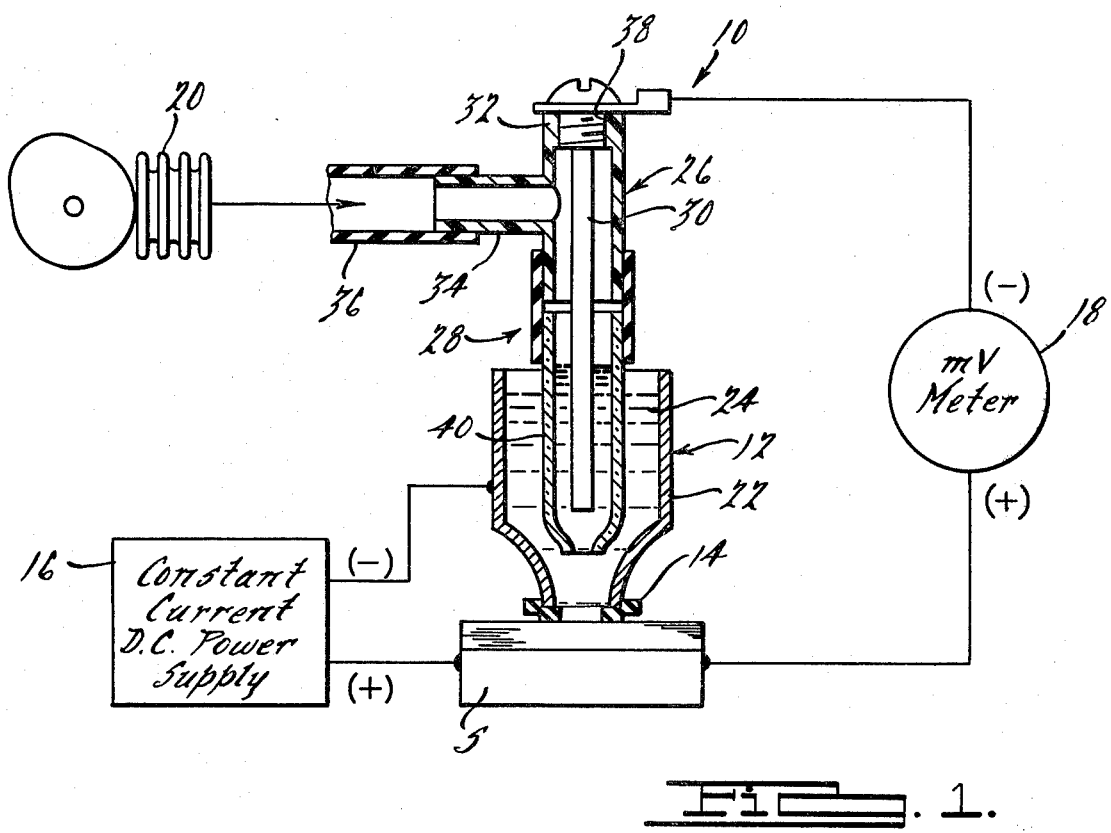
FIG. 1 is a schematic view of the testing apparatus of the present invention.

Referring now to the drawings, and in particular to FIG. 1, the testing apparatus of the present invention is indicated generally by the numeral 10. It is illustrated schematically as comprising an electrically conductive deplating cell 12 configured for mounting on a multilayer plated sample S in a fluidly sealed relationship as through a gasket 14, which also exposes a known area (such as a circular area of 0.125 inch diameter) of deposit surface, a constant current D.C. power supply 16 connected with the indicated polarity to pass current through the sample S, while in the anode, the electrolyte, and the cell 12 which is the cathode, a voltage measuring device 18, and agitator means such as a pump 20, which mixes the electrolyte to prevent concentration polarization, is fluidly connected to the cell 12.

The deplating cell 12 may be similar in construction to commercially available deplating test cells well known to those skilled in the plating arts. It is illustrated in FIG. 1 as a cup-shaped shell member 22, engaging the gasket 14 and providing means for electrically connecting the negative side of the power supply 16 to the cell 12, a suitable electrolyte 24 (to be later defined) received in the shell member 22, and a reference electrode assembly 26 supported (by means not shown) for immersion in the electrolyte 24.

The reference electrode assembly 26 is illustrated as comprising a generally T-shaped housing assembly 28 and a metal reference electrode 30. The housing assembly includes an upper connector portion 32 providing a port 34 for connection to the agitator pump 20 as through tubing 36 and a threaded portion 38 for mounting the reference electrode 30. The housing assembly 28 further includes a lower tubular portion 40, preferably formed of a chemically inert electrically nonconductive material such as glass or plastic, which surrounds the lower portion of the reference electrode 30 both of which are in contact with the electrolyte 24.

When current is passed through the cell 12, electrolyte 24, and sample S at a given chosen level, such as at a current density of 100–400 amperes/ft$^2$, with the sample S being the positive component and the cell the negative component, the electrodeposited plating on the sample S is anodically stripped away. By concurrently measuring the voltage between the sample S and the reference electrode 30 the level of electrochemical dissolution activity of the deposit layers may be established since it is known that the measured voltage is a function of the activity level of the various multilayer deposits. The reference electrode 30 is used in the cell 12 so that potential differences between layers of the sample S can be measured without concern for effect of voltage variations in the power supply which are not related to the dissolution activity. Since the different layers of a multilayer sample are expected to have different levels of electrochemical dissolution activity then different voltages or potential values can be observed for each layer. Recording the varying voltage levels on a time base, as through use of a known strip chart recorder incorporating the voltage measurement device 18 permits computation of layer thicknesses through use of Faraday's Laws. It simultaneously yields an indication of the difference in potential between different layers and relative polarity of the layers of the sample S so that a simple and effective means of determining the corrosion protection provided by the deposit layers to the sample S is provided.

Figure 2:
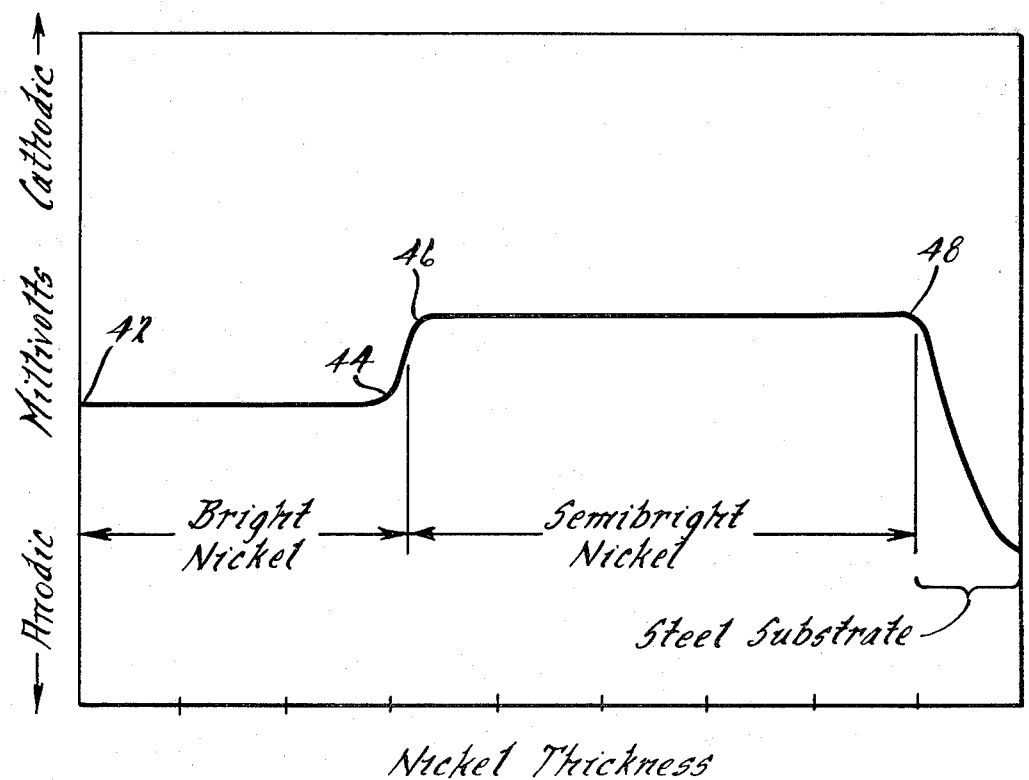
FIG. 2 is a typical curve that can be generated in testing according to the present invention.

Turning now to FIG. 2, a graphic representation, such as can be produced using a strip chart recorder as the voltage measuring device 18, is shown for an example in which a sample S consisting of two nickel layers, one bright and one semibright, are plated on a steel substrate. In this environment it has been established that the electrolyte 24 should be chosen to provide one hundred percent anode efficiency for stripping. Although others may be suitable, one used successfully was the following:

| | |
|---|---|
| $NiCl_2 \cdot 6H_2O$ | 300g/l |
| NaCl | 50g/l |
| $H_3BO_3$ | 25g/l |

Other acceptable solutions that have been found are hydrochloric acid in a 10% by volume solution and a solution of hydrochloric acid (5 vol. %) and $NiCl_2 \cdot 6H_2O$ (10 g/l)

It was also established that more dilute solutions such as

| | |
|---|---|
| NaCl | 30g/l |
| $Cu(NO_3)_2 \cdot 3H_2O$ | 0.2g/l | which have been used for open circuit potential measurements (as reported by A. H. DuRose in *Proceedings of the American Electroplaters Society*, 47,p. 83, 1960) are unsuitable because of low conductivity and that electrolytes containing active sulphur compounds such as NaSCN are unsuitable since the sulphur affects the dissolution activity of nickel deposits preventing measurement of low (less than approximately 250 multivolts) interlayer potentials.

Other limitations on the electrolyte choice have been found when a silver wire was chosen for reference electrode 30. This electrode choice has been found advantageous since it rapidly becomes a silver-silver chloride electrode when used with chloride containing electrolytes. However, it has been found that ions which react with silver or silver chloride, e.g., ammonium, nitrate, thiosulphate ions in the electrolyte interfere with the test when this reference electrode material is used.

Turning again to FIG. 2 the curve A illustrates the simultaneous measurement of electrochemical potential and layer thickness for a typical duplex nickel plated steel object. After first removing the chromium layer, should one be present, the thickness of the bright nickel layer is measured along the time base shown as the ordinate of the curve A here between points indicated by the numerals 42,44. Subsequently, the thickness of the semibright nickel layer is measured as between the points indicated by the numerals 46,48. The portion of the curve A to the right of point 48 shows the voltage dropping off sharply as the steel substrate is encountered. The voltage values measured on the abscissa of the curve A are indicative of the dissolution activity of the various layers. It was found that potential differences between bright and semibright layers on the order of at least 100 mV or preferably 125 mV with the bright nickel more active (lower voltage) then the semibright nickel indicate a sample which will exhibit corrosion resistance characteristics of good duplex nickel deposits. Conversely, potential differences between bright and semibright nickel layers of less than about 100 mV indicate sample deposits with corrosion properties more like single layer nickel deposits, especially if the potential difference is about 60 mV or less.

While only one apparatus and example for practice of the present invention have been described those skilled in the plating arts will appreciate that others may be possible without departing from the scope of the appended claims.

What is claimed is:

1. A method for measuring the thickness of individual layers of a multilayer electrodeposit while simultaneously measuring the electrochemical potential difference and determining the polarity between said layers comprising the steps of:
    A. placing an anodic sample of known area of said multilayer electrodeposit, a cathode, and a reference electrode in contact with an electrolyte solution;
    B. passing a constant direct current through said sample, said cathode, and said electrolyte solution;
    C. measuring the potential between each layer of said sample and said reference electrode as a function of time and computing therefrom the thickness of said individual layers using Faraday's Laws; and
    D. simultaneously with said measuring step, observing and computing the electrochemical potential difference between said layers and observing the polarity of the layers with respect to each other.

2. A method for measuring the thickness of individual nickel layers of a multilayer nickel electrodeposit and simultaneously measuring the electrochemical potential difference and determining the polarity between said layers comprising the steps of:
    A. placing an anodic sample of known area of said multilayer electrodeposit, a cathode, and a reference electrode in contact with an electrolyte solution;
    B. passing a constant direct current through said sample, said cathode, and said electrolyte solution;
    C. measuring the potential between each layer of said sample and said reference electrode as a function of time and computing therefrom the thickness of said individual layers using Faraday's Laws; and
    D. simultaneously with said measuring step, observing and computing the electrochemical potential difference between said layers and observing the polarity of the layers with respect to each other.

3. The method as defined in claims 1 or 2 wherein said electrolyte is substantially free of active sulphur compounds or ammonium salts.

* * * * *